United States Patent [19]

Oberholz et al.

[11] Patent Number: 5,227,480

[45] Date of Patent: Jul. 13, 1993

[54] PROCESS FOR THE PREPARATION OF ALKYL GLYCOSIDES AND ALKYL OLIGOGLYCOSIDES

[75] Inventors: Alfred Oberholz, Marl; John Kahsnitz, Haltern; Stefan Schmidt, Recklinghausen, all of Fed. Rep. of Germany

[73] Assignee: Huels Aktiengesellschaft - PB 15, Marl, Fed. Rep. of Germany

[21] Appl. No.: 779,233

[22] Filed: Oct. 18, 1991

[30] Foreign Application Priority Data

Oct. 26, 1990 [DE] Fed. Rep. of Germany ....... 4034074

[51] Int. Cl.$^5$ ............................................. C07H 15/04
[52] U.S. Cl. .................................. 536/18.5; 536/18.6; 536/124
[58] Field of Search ............... 536/18.6, 18.5, 124

[56] References Cited

U.S. PATENT DOCUMENTS

| | | | |
|---|---|---|---|
| H619 | 4/1989 | McDaniel et al. | 536/18.6 |
| 4,511,739 | 4/1985 | Sauer et al. | 568/473 |
| 4,554,054 | 11/1985 | Coyle | 562/600 |
| 4,713,447 | 12/1987 | Letton | 536/18.6 |
| 4,721,780 | 1/1988 | McDaniel et al. | 536/18.6 |
| 4,866,207 | 9/1989 | Jonckers et al. | 564/71 |
| 4,996,306 | 2/1991 | McDaniel et al. | 536/120 |
| 5,079,350 | 1/1992 | Fujita et al. | 536/18.6 |

FOREIGN PATENT DOCUMENTS

| | | |
|---|---|---|
| 0231890 | of 0000 | European Pat. Off. . |
| 0099183 | 6/1983 | European Pat. Off. . |
| 3623246 | of 0000 | Fed. Rep. of Germany . |

*Primary Examiner*—Johnnie R. Brown
*Assistant Examiner*—Everett White
*Attorney, Agent, or Firm*—Oblon, Spivak, McClelland, Maier & Neustadt

[57] ABSTRACT

Alkyl glycosides and alkyl oligoglycosides of low iodine color number can be prepared by acid-catalyzed condensation of saccharides in an aqueous solution with short-chain alcohols at elevated temperature in a counter-current reaction column.

5 Claims, 1 Drawing Sheet

PROCESS FOR THE PREPARATION OF ALKYL GLYCOSIDES AND ALKYL OLIGOGLYCOSIDES

FIELD OF THE INVENTION

The invention relates to a process for the preparation of alkyl glycosides and alkyl oligoglycosides, in which saccharides are reacted in aqueous solution with alcohols having 1 to 6 carbon atoms at elevated temperature with acid catalysis.

DISCUSSION OF THE BACKGROUND

Alkyl glycosides and alkyl oligoglycosides having alkyl radicals of from 1 to 6 carbon atoms are intermediates in the preparation of long-chain alkyl polyglycosides, which have surfactant properties. According to EP-A-0,099,183, the preparation of alkyl glucosides from aqueous saccharides and short-chain alcohols is carried out at elevated pressure and, preferably, in the presence of cosolvents. The reaction can be carried out in a stirred or tubular reactor, it being preferred to carry out the reaction in a stirred reactor.

In DE-A-3,623,246, no cosolvent is required in the reaction of aqueous saccharide with short-chain alcohol. The reaction can be carried out in stirred reactors operating continuously or batchwise. Preferably, a cascade of stirred reactors is used. However, the products of this process do not satisfy the high requirements of some applications with respect to colour.

SUMMARY OF THE INVENTION

The object of the present invention is to prepare alkyl glycosides and alkyl oligoglycosides of satisfactory colour from saccharides in aqueous solution and alcohols having 1 to 6 carbon atoms without using superatmospheric pressure and foreign cosolvents. This object is achieved by carrying out the reaction in a counter-current reaction column.

DETAILED DESCRIPTION OF THE PREFERRED EMBODIMENTS

Figure 1:
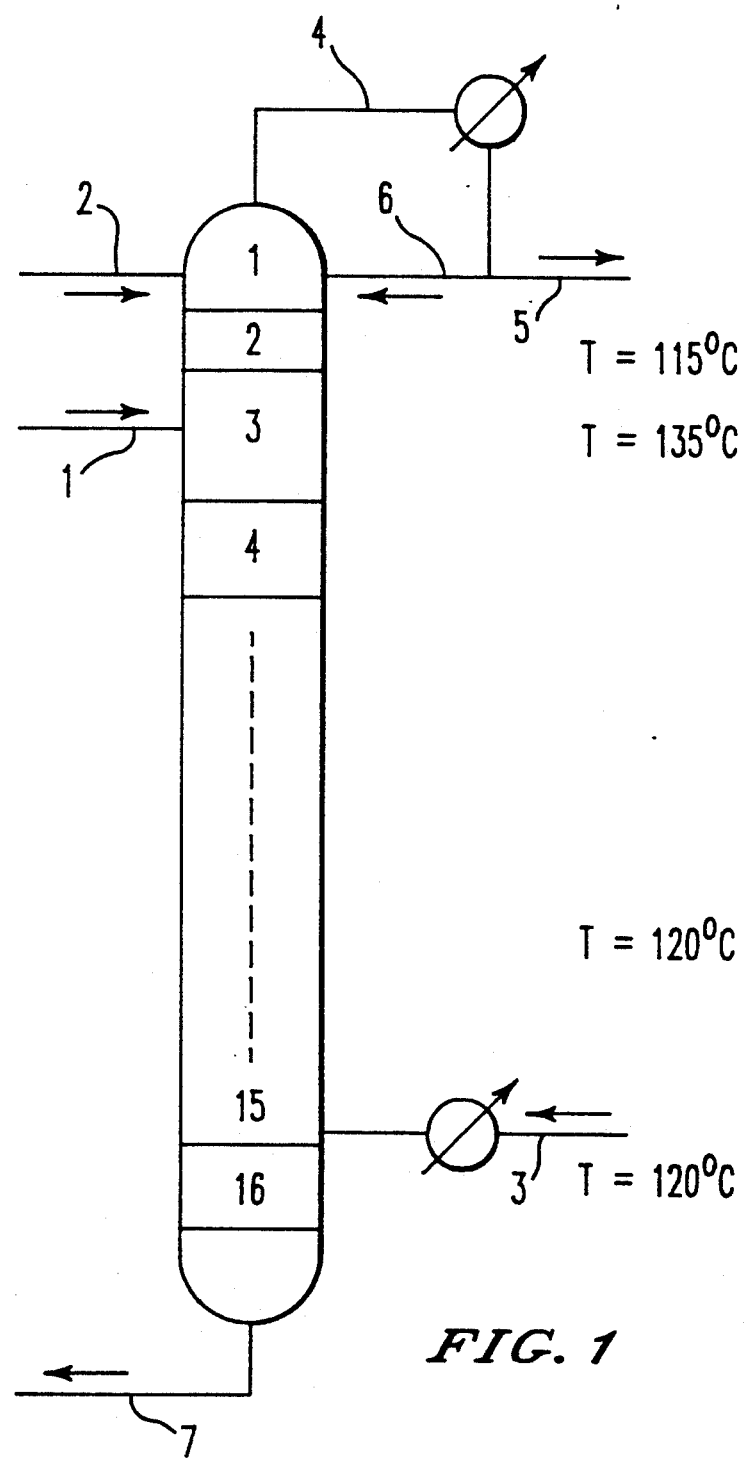
FIG. 1 is a schematic representation of a bubble-cap column having 16 actual plates.

The alkyl oligoglycosides of the present invention, have a degree of oligomerization in the range from 1 to 4. It has bee found that products having surprisingly low iodine numbers of 15 or less can be prepared in high yield by using counter-current reaction columns.

Suitable starting saccharides are mono-, di- or oligosaccharides. Examples of these are glucose, mannose, galactose, gulose, allose, ribose, arabinose, xylose or saccharose. Starch hydrolysis products can also be used. In general, pumpable aqueous solutions are used. Saccharide syrups containing 10 to 75% of water are preferably used in this process. Dextrose syrups having water contents of 50 to 70% are very particularly preferred.

Examples of suitable alcohols are methanol, ethanol, propanol, isopropanol, n-butanol, isobutanol, pentanol, hexanol or cyclohexanol. Preferably, n-butanol is used.

Suitable catalysts are in particular mineral acids, such as sulphuric or phosphoric acid and strong organic acids, such as benzenesulphonic acid, cumenesulphonic acid or p-toluenesulphonic acid. Owing to their lower corrosiveness, organic acids are preferably used as catalysts. In most cases, the catalysts are added as an aqueous or as an alcoholic solution.

Suitable counter-current reaction columns are the customary columns, such as bubble-cap, sieve-plate, tunnel-cap or packed columns. The columns preferably have 3 to 40 actual plates. Of these, columns having 10 to 20 actual plates are particularly preferred.

In the counter-current reaction column, the temperature is set to a value at which the saccharide, alkyl glycoside and alkyl oligoglycoside can flow downward in the liquid phase and at which alcohol and water can be discharged at the column head in the gas phase. In most cases the reaction temperature is 70° to 150° C. and is preferably set between 90° to 140° C.

Although the reaction can also be carried out at superatmospheric pressure, the reaction is generally carried out at atmospheric pressure or at a slight vacuum of up to about 0.05 MPa.

The present process does not require any foreign cosolvents and no superatmospheric pressure. No complicated equipment is necessary. The apparatus is simpler than a conventional cascade of stirred reactors. No mechanical energy is required. In addition, compared with the cascade process, the present invention yields products of improved colour in combination with a high conversion.

According to the invention, the general procedure is such that the aqueous saccharide solution, which may also contain alcoholic alkyl glycoside, and the catalyst solution are introduced into the upper portion of the counter-current reaction column. The alcohol is introduced in the form of vapour into the lower portion of the column. After the acetalization or glycosylation reaction, unconverted alcohol and water are discharged at the top of the column. If phase separation takes place upon cooling the top product, the alcohol can be recycled directly or after work-up. It is also possible to introduce the alcohol together with fresh alcohol in the form of vapour into the lower portion of the column. The reaction products, alkyl glycosides and alkyl oligoglycosides, are isolated at the bottom of the column.

If alkyl glycoside is intended to be introduced into the upper portion of the column, a portion of the reaction product can be recycled for this purpose. However, it is also possible to prepare the alkyl glycoside in a preliminary reactor step from saccharide and alcohol using a stirred reactor or cascade of stirred reactors, for example. For this preliminary reaction one can use the alcohol which is obtained at the column head, after the water has been separated off.

In the examples which follow, percentages are by weight, unless stated otherwise.

Other features of the invention will become apparent in the course of the following descriptions of exemplary embodiments which are given for illustration of the invention and are not intended to be limiting thereof.

EXAMPLE 1

The reaction is carried out in a bubble-cap column schematically shown in FIG. 1 (16 actual plates, static hold-up=200 ml/plate, internal plate diameter D=80 mm, height h=100 mm/plate). Via line 1, 2.3 mol/h of glucose as a 55% aqueous solution and 8 l/h of 35% butyl glucoside in butanol (10.9 mol/h) are introduced to the third plate. 108 ml/h of 10% p-toluenesulphonic acid in butanol are introduced at the column head via line 2. In addition, 1.3 l/h of butanol (14.4 mol/h) are introduced as superheated vapour into the column at the 15th plate. The column is operated at the temperatures given in FIG. 1.

A butanol/water mixture is discharged via line 4 as distillate. After cooling and phase separation, water is separated off via line 5, while butanol is returned to the column via line 6. 10 l/h of butyl glucoside in butanol having a glucose content of <0.5% and a water content of <0.6% are obtained from the cold still pot of the column via line 7. Iodine colour number: <15

COMPARATIVE EXAMPLE A

Preparation of butyl glucoside in a cascade of stirred reactors.

0.8 l/h of 70 glucose syrup (3.45 mol/h), 1.5 l/h of butanol (16.8 mol/h) and 1% by weight of p-toluenesulphonic acid per hour, relative to the total amount of feed materials, are introduced into a 2-step cascade of stirred reactors comprising two 5 liter stirred reactors. The stirred reactors are heated to the boiling temperature, as a result of which a butanol/water mixture distills off continuously. The distillate is separated into a water phase and a butanol phase, the butanol phase being recycled into the reactors and the water phase being discarded. The product from the second reactor is an approximately 35% by weight solution of butyl glucoside in butanol having a glucose content of <0.5% and a water content of <0.6%.

Iodine colour number: >300

We claim:

1. In a process for the preparation of alkyl glycosides and alkyl oligoglycosides by acid-catalyzed acetalization of saccharides in aqueous solution with alcohols having 1 to 6 carbon atoms at 70°–150°, the improvement comprising: running the acetalization reaction in a counter-current reaction column.

2. Process according to claim 1, wherein a saccharide syrup containing 10 to 75% of water is used.

3. Process according to claim 2, wherein a dextrose syrup containing 50 to 70% of water is used.

4. Process according to claim 1, wherein the alcohol used is n-butanol.

5. Process according to claim 1, wherein the reaction is carried out in a column having 3 to 40 actual plates.

* * * * *